United States Patent [19]

Crabb et al.

[11] Patent Number: 4,650,333
[45] Date of Patent: Mar. 17, 1987

[54] SYSTEM FOR MEASURING AND DETECTING PRINTED CIRCUIT WIRING DEFECTS

[75] Inventors: Robert M. Crabb, Endicott; Steven M. DeFoster, Binghamton; Norman E. Rittenhouse, Endicott; Mark A. West, Binghamton; Richard A. Ziegler, Vestal, all of N.Y.

[73] Assignee: International Business Machines Corporation, Armonk, N.Y.

[21] Appl. No.: 599,422

[22] Filed: Apr. 12, 1984

[51] Int. Cl.⁴ .............................................. G01B 11/24
[52] U.S. Cl. ..................................... 356/376; 356/237; 356/381; 358/106
[58] Field of Search ..................... 350/358; 356/1, 237, 356/371, 376, 381; 358/101, 106, 107

[56] References Cited

U.S. PATENT DOCUMENTS

| | | | |
|---|---|---|---|
| 3,669,540 | 8/1970 | Rattman et al. | 356/4 |
| 3,699,304 | 10/1972 | Baldwin, Jr. et al. | 219/121 |
| 3,712,466 | 1/1973 | Aubry et al. | 209/73 |
| 3,713,739 | 1/1973 | Zarezankov et al. | 356/163 |
| 3,834,819 | 9/1974 | Montone | 356/381 |
| 3,844,799 | 10/1974 | Underkofler et al. | 106/1 |
| 4,017,188 | 4/1977 | Sawatari | 356/120 |
| 4,028,728 | 6/1977 | Sharp | 356/237 |
| 4,152,467 | 5/1979 | Alpaugh et al. | 427/8 |
| 4,158,507 | 6/1979 | Himmel | 356/376 |
| 4,188,544 | 2/1980 | Chasson | 356/376 |
| 4,339,664 | 7/1982 | Wiklund et al. | 250/577 |
| 4,349,277 | 9/1982 | Mundy et al. | 356/376 |
| 4,455,485 | 6/1984 | Hosaka et al. | 350/358 |
| 4,472,056 | 9/1984 | Nakagawa et al. | 356/376 |
| 4,498,778 | 2/1985 | White | 356/107 |
| 4,529,316 | 7/1985 | DiMatteo | 356/376 |
| 4,573,073 | 2/1986 | Corby, Jr. | 358/107 |
| 4,589,140 | 5/1986 | Bishop et al. | 358/106 |

FOREIGN PATENT DOCUMENTS 2554086  6/1977  Fed. Rep. of Germany.
3204086  8/1983  Fed. Rep. of Germany ...... 356/237

OTHER PUBLICATIONS

Sterling, Proc. Soc. Photo-Opt. Instrum. Eng., vol. 281, Techniques and Applications of Image Understanding, p. 182, 1981.
Hauge, *IBM Technical Disclosure Bulletin*, vol. 21, No. 2, Jul. 1978, p. 884.
Kapur, *IBM Technical Disclosure Bulletin*, vol. 21, No. 11, Apr. 1979, p. 4429.
"Noncontact Test System", S. H. Campbell et al, IBM Technical Disclosure Bulletin, vol. 14, No. 12, May 1972.

Primary Examiner—F. L. Evans
Assistant Examiner—Joel L. Harringa
Attorney, Agent, or Firm—Mark Levy

[57] ABSTRACT

A non-contact system for detecting printed circuit wiring defects and for measuring circuit feature height relative to a substrate. The system has an energy source for illuminating the substrate and circuit features and a scanner for both instantaneously receiving energy reflected from the substrate and circuit features and for generating a signal in response to the reflected energy, which signal is adapted to vary with the intensity of the reflected energy. An analyzer is connected to the scanner for correlating the generated signal to a measurement representative of the height of the circuit features relative to the substrate. Variations and non-uniformity of the substrate surface due to bending, warpage or other causes can be accounted for so as to provide an accurate measurement of the height of a circuit feature relative to the substrate surface on which it is mounted.

19 Claims, 10 Drawing Figures

SYSTEM FOR MEASURING AND DETECTING PRINTED CIRCUIT WIRING DEFECTS

BACKGROUND OF THE INVENTION

The present invention relates to a system for measuring the height of circuit features on a substrate and more particularly to a non-contact system for detecting and measuring electrical conductor defects on a printed circuit board.

Inspecting manufactured articles for defects and for proper placement in larger assemblies is often a time consuming, yet necessary step in the production of complex devices. In the field of electronic components, inspection and measuring systems have relied on human inspectors using microscopes or other more sophisticated equipment.

Such systems are, of course, labor intensive and prone to human operator error, being dependent upon eyesight and judgment. Moreover, in the course of inspecting and measuring components a potential exists for damaging the articles themselves, due to physical handling thereof. In fact, in certain procedures for determining the integrity of wiring fabrication, so called destructive testing is undertaken on samples. If a sample fabricated at the same time and in the same manner as the manufactured product passes such a destructive testing procedure, it is assumed that the product itself is defect free. This assumption may be unwarranted in some cases.

A need has arisen for a procedure to inspect articles quickly, minimizing both manual labor and the possibility of damage to the articles during the inspection process, while increasing accuracy of the inspection. In particular, a non-contact procedure is preferred for inspecting and measuring the size and orientation of electronic components as well as for detecting wiring defects, if any, on a printed circuit board.

Dimensions of electronic components and thickness of wires or leads continue to decrease. Concomitantly, the criticality of positions of components and wires relative to the board or substrate on which they are mounted continues to increase. Accordingly, inspection procedures must be increasingly accurate.

It can be appreciated that even relatively small defects in wiring become a greater problem as the size of the wire decreases. In previous systems in which wiring dimensions were relatively great, small defects therein did not significantly affect performance of the overall system. With the ever decreasing size of wires used in sophisticated computing system sub-assemblies, however, relatively minor defects can result in performance degradation. Thus, defects that may not have even been detected in previous inspection systems must now be detected and corrected to ensure proper operation of the manufactured assemblies.

A system for measuring the two-dimensional size of geometrical features and/or their locations is described in "Noncontact Test System", by S. H. Campbell, et al, IBM Technical Disclosure Bulletin, Vol. 14, No. 12, May 1972. This system uses a CPU for analyzing data generated by a scanner. The scanner receives light reflected from an illuminating source.

A test system for measuring placement of circuit lines on a substrate is described in copending application Serial No. 460,702, filed Jan. 24, 1983, for "Apparatus for Automatic Optical Property Testing" and assigned to the assignee of the present application. In that system, an optical scanning head comprises two arrangements of linear diode arrays positioned adjacent one another. One diode array receives light reflected from a base plate while the other diode array receives light reflected from the surface of a conductor, provided that the latter is at the desired nominal height. Detected defects are marked and may be displayed on a TV screen.

Light has also been used heretofore to detect defects in certain goods by responding to non-uniformities in light reflectance therefrom. U.S. Pat. No. 3,712,466, issued to Aubry, et al, for example, teaches a system for optically inspecting shell casings which are conveyed successively over a predetermined path. A photocell and lens system detects reflected light from the shell and determines, by non-uniformity in the reflected light level, whether a flaw or defect exists.

U.S. Pat. No. 4,339,664, issued to Wiklund, et al, teaches a method and apparatus for topographic measurements of a charged mass in a blast furnace. A distance meter is provided near the top of the furnace for detecting direct reflection against the upper surface of the charge. The distance meter has an aiming device so that measurements of selected parts of the surface can be measured.

Devices have also been used heretofore to measure the height of an object or target relative to a surface. Such devices are often used in radar systems. Visible light may also be used to measure the distance between such a target and a surface. U.S. Pat. No. 3,669,540, issued to Rattman, et al, for example, discloses one such system in which a laser on board a helicopter is used to measure the depth of the ocean or of a submerged object. In this aforementioned reference, the altitude of the helicopter is determined by measuring the time interval between the transmission of a laser pulse and the detection of the resulting energy reflected from the ocean surface. The time interval between the transmitted laser pulse and the detected reflected energy from the surface of the ocean is compared to the time interval between the transmitted laser pulse and the detected reflected energy from the ocean floor or submerged object in order to arrive at the relative depth thereof. Such a system requires accurate time measurement, using the speed of light as a factor.

Systems have also been disclosed for use with considerably more complex light detecting apparatus. For example, U.S. Pat. No. 4,349,277, issued to Mundy, et al, discloses a parallax system for measuring and mapping a surface profile in which a light beam is split into two beams, each having a different frequency. Two images are projected onto a color pattern and a shift in the relative distance between the pattern and the light source can be detected, indicating roughness variations.

U.S. Pat. No. 4,017,188, issued to Sawatari, discloses an optical system for determining surface roughness which includes two light detectors that view two separate images of a spot focused by a lens through a slit. The respective detector signals are divided to produce signals corresponding to the ratio thereof, which in turn correspond to variations of surface height occurring as the illuminated spot is scanned across the surface.

Similarly, U.S. Pat. No. 3,713,739, issued to Zarezankov, et al, discloses a system in which a beam of light strikes each of the opposite surfaces of a rolled product, producing an image onto two separate screens of electron beam tubes. The distance between the images is measured and used to derive the distance of linear cross-sectional dimensions of the rolled product.

It would be advantageous to provide an optical non-contact system for measuring the height of circuit features on a substrate without the need for complex optical or time measurement apparatus.

It would also be advantageous to provide a system for three-dimensional optical measurement with the use of only one imaging device capable of distinguishing substrate energy reflectance from circuit feature energy reflectance.

It would further be advantageous to perform such measurement independent of light reflection time and/or substantially instantaneously.

It would also be advantageous to measure the height of such circuit features relative to a substantially planar but non-uniform substrate on which they are mounted.

It would also be advantageous to use the level of intensity of reflected light both to determine the height of circuit features and to detect and compensate for non-linearities in the upper surface of the substrate on which they are mounted.

SUMMARY OF THE INVENTION

In accordance with the present invention, there is provided a non-contact system for detecting printed circuit wiring defects and for measuring circuit feature height relative to a substrate. The system has an energy source for illuminating the substrate and circuit features and a scanner for both instantaneously receiving energy reflected from the substrate and circuit features and for generating a signal in response to the reflected energy, which signal is adapted to vary with the intensity of the reflected energy. An analyzer is connected to the scanner for correlating the generated signal to a measurement representative of the height of the circuit features relative to the substrate.

Moreover, variations and non-uniformity of the substrate surface due to bending, warpage or other causes can be accounted for so as to provide an accurate measurement of the height of a circuit feature relative to the substrate surface on which it is mounted.

BRIEF DESCRIPTION OF THE DRAWINGS

A complete understanding of the present invention may be obtained by reference to the accompanying drawings, when taken in conjunction with the detailed description thereof and in which.

DETAILED DESCRIPTION OF THE PREFERRED EMBODIMENT

Figure 1:
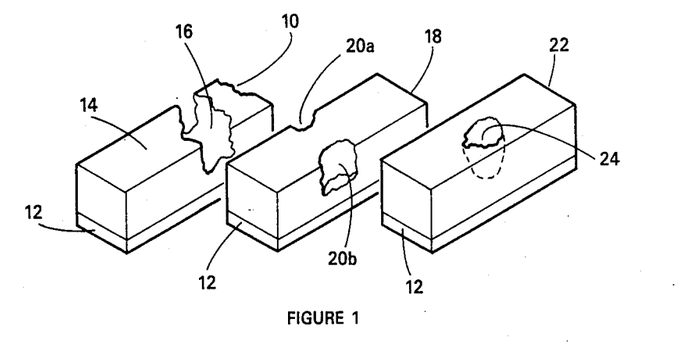
FIG. 1 is an exploded perspective view of a portion of three additively plated circuit wires with defects therein.

Referring now to FIG. 1, there is shown a greatly exploded perspective view of three circuit features, such as electrically conductive wires fabricated by an additive plating process, such as is described in U.S. Pat. Nos. 3,844,799 issued to Underkofler, et al and 4,152,467 issued to Alpaugh, et al, both of which are hereby incorporated by reference. It should be understood, however, that the product of any other type of additive process or any other circuit fabrication process may be prone to the defects described herein, all of which are detectable and measurable by the present invention.

The circuit features shown in FIG. 1 have three-dimensional defects therein. Circuit feature 10 includes a base material 12 such as copper, which is normally bonded to a substrate, not shown, and then appropriately etched. During an additive plating process, more material 14 is then deposited onto the etched base layer 12. The added material 14 is electrically conductive, such as copper in the preferred embodiment. Occasionally during the printed circuit fabrication process, an irregularly shaped three-dimensional defect 16 may occur due to any one of a number of causes well known in the art of additive plating, for example. The defect identified by reference numeral 16 is commonly referred to as "dish down".

As another example of defects, circuit feature 18 is also mounted on a base material 12 and has a pair of defects 20a and 20b commonly known as "neck down". Finally, circuit feature 22, mounted on a base material 12, has a defect 24 commonly known as "plating void" or "pinhole".

It should be understood that while the aforementioned defects occur most commonly, other types of defects, such as nodules formed from excess copper and the like, may also be formed during an additive process. The present invention is intended to detect and measure any such defects, however formed.

Figure 2:
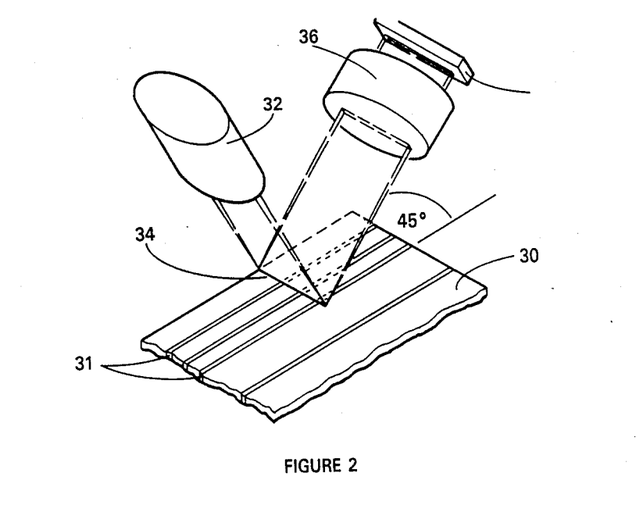
FIG. 2 is a perspective view of a light slit projected onto a circuit board and circuit features.

Referring now also to FIG. 2, there is shown a substrate 30, such as a printed circuit board, on which are placed or formed circuit features 31 such as lines of electrical conductance. These circuit features 31 may be embedded or laminated onto the printed circuit board 30. The circuit features 31 may have defects, not shown in FIG. 2, as hereinabove described, which are detectable and measurable by the present invention.

A slit of light is generated by a light source, not shown, through a suitable optical lens assembly 32. The optical lens assembly 32 may be a multiple element lens or a series of lenses as are commonly used and well known in the art. In the preferred embodiment, cylindrical optics 32 are used to project a slit of light 34 approximately 0.5 mils (0.0005 inches) wide and 1.1 inches long. The light slit 34 in the preferred embodiment is projected onto the printed circuit board 30 such that the angle of incidence is 45° relative to the plane thereof in order to provide light which represents the true proportion of features measured along the height dimension. It should be understood, however, that an angle less than or greater than 45° may be used to optimize contrast as well as to satisfy other design considerations.

A collector lens 36 is disposed opposite the light lens 32 for receiving reflected light from the printed circuit board 30 also at an angle of 45° relative to the plane thereof. Optically related to the collector lens 36 is a charged coupled device (CCD) 38 or imaging device, such as is manufactured by Fairchild Camera and Instrument Corp. as Model No. 1600R, for receiving the image of the slit 34 projected onto the board 30 and reflected therefrom.

The board 30 is adapted to move in directions parallel to the plane thereof (i.e., in the X and Y directions) relative to the light source and optical lens 32 by suitable means. It will be appreciated, however, that the board 30 may be stationary while the lens 32 is passed thereover. Similarly, although one CCD 38 is shown in FIG. 2, it should be understood that the system may be adapted for use with an array of light detecting devices, such as CCD's or the like. The array of CCD's may be polled so that each CCD device is individually accessed and the data therefrom is appropriately organized in a format that is usable in future analysis.

Figure 3:
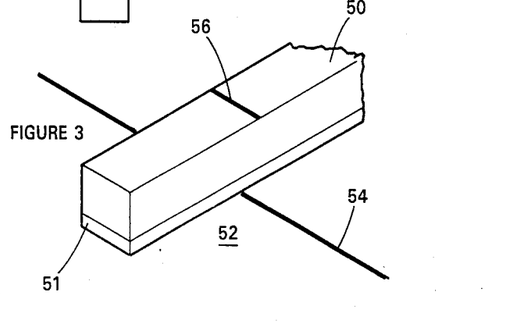
FIG. 3 is a perspective view of a light slit projected onto a circuit feature.

Referring now also to FIG. 3, there is shown an exploded perspective view of an electrical conductor 50 and base 51 plated onto a substrate 52. A light slit 54 is projected onto the substrate 52. The portion of the light slit 54 that is interrupted by the upper surface of the conductor 50 is identified by reference numeral 56.

Figure 4:
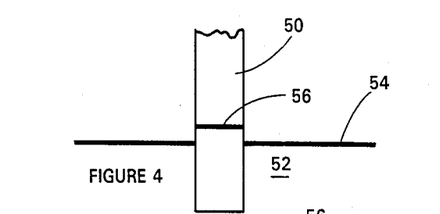
FIG. 4 is a top plan view of a light slit projected onto a circuit feature.

Referring now also to FIG. 4, there is shown a top view of the light slit 54 projected onto both the electrical conductor 50 and the substrate 52. When the light slit 54 is projected at an angle of 45° relative to the plane of the printed circuit board substrate 52 as shown in FIG. 2, the distance X between the light slit 56 projected onto the conductor 50 and the light slit 54 projected onto the substrate 52 is equal to the height of the conductor 50 relative thereto.

Figures 5, 6:
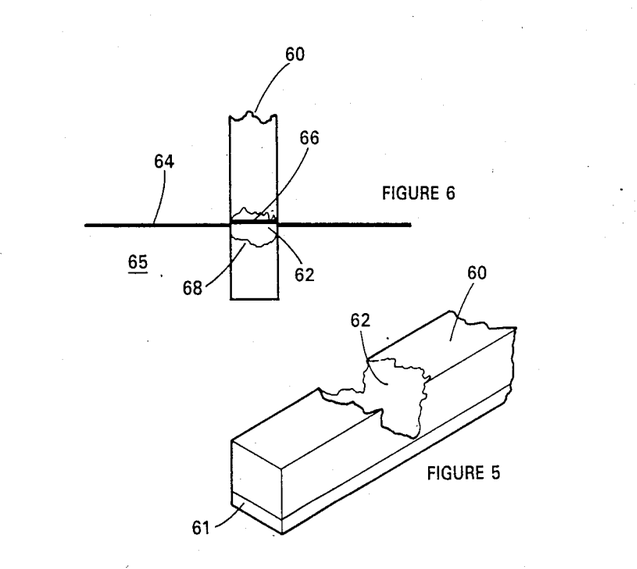
FIG. 5 is a perspective view of a light slit projected onto a circuit feature having a defect therein.
FIG. 6 is a top plan view of a light slit projected onto a circuit feature having a defect therein.

Referring now also to FIG. 5, there is shown another electrical conductor circuit feature 60 and its base 61 in which an irregularly shaped defect 62 of the dish down variety has occurred.

Referring now also to FIG. 6, there is shown a top plan view of a light slit 64 projected onto a substrate 65 on which is located the circuit feature 60. The light slit on the top surface of the circuit feature 60 is identified by reference numeral 66. The portion of the defect 62 onto which the light slit 66 is projected is identified by reference numeral 68.

Figure 7:
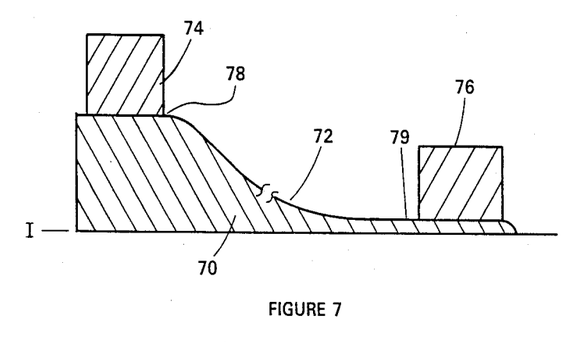
FIG. 7 is a cross-sectional view of a portion of a non-uniform printed circuit board.

Referring now also to FIG. 7, there is shown a cross-sectional view of a substrate or printed circuit board 70 with circuit features 74 and 76 located thereon. The circuit board 70 has an upper surface 72 which is warped along the Z-axis (vertical dimension). That is, the upper surface 72 of the printed circuit board 70 is higher on one side 78 than it is on the other side 79.

Circuit features 74 and 76 both have equal dimensions in the Z direction, but are situated on the substrate 70 so that the overall height of circuit feature 74 measured from an initial reference level I is greater than the overall height of circuit feature 76, measured from initial level I. Thus, it can be seen that to determine the height dimension of each circuit feature 74 and 76, the height of the upper surface of the substrate at reference numerals 78 and 79 proximate the base of respective circuit features 74 and 76 must also be determined and subtracted from the overall measurements of circuit feature upper surface, all relative to initial level I.

Figure 8:
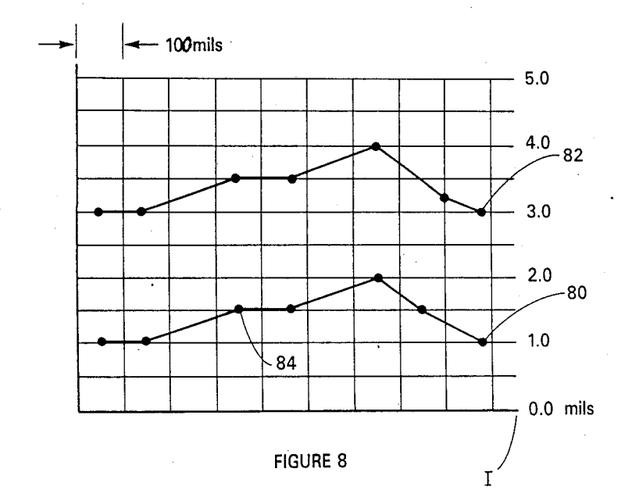
FIG. 8 is a graphical piece-wise analysis of the substrate base and circuit feature height on a non-uniform circuit board.

Referring now also to FIG. 8, there is shown a graphical representation of substrate height and height of a circuit feature over a horizontal distance on an uneven or non-uniform substrate 30. Line 80 is a profile of the upper surface of the substrate 30. Line 82 represents the topmost surface of the circuit feature. All height measurements are taken relative to the initial reference level I.

The graph in FIG. 8 is generated by taking one-inch long height slices along the area to be measured. In the preferred embodiment, 12 slices, separated from one another by a separation distance of 0.5 mils, are required to bracket the distance from below the upper surface of the substrate 30 to above the upper surface of the circuit feature.

It should be appreciated, however, that arbitrary separation distances between height slices other than 0.5 mils can be chosen in other situations, depending upon the size of the circuit features being measured as well as upon the degree of precision required. Moreover, the separation distances chosen need not be uniform in all situations. Similarly, the number of height slices used in other situations may vary according to prevailing spatial and precision parameters.

In the example depicted in FIG. 8, light is not reflected from the substrate 30 at a height level of 0 mil or 0.5 mils relative to initial reference level I. This is to be expected, as initial level I is below the upper surface of the substrate 30 and the plane at that height is imaginary as far as the image receiving CCD 38 is concerned. The image at initial level I (0 mil) is non-existent. Accordingly, neither the base line 80 nor the upper surface copper line 82 appears at 0 mil or 0.5 mils. At a height of 1.0 mil, however, the light slit 34 is reflected from the upper surface of the substrate 30 and registers on the CCD 38 in the leftmost column of the graph.

As the height dimension is incrementally increased at 0.5 mil separation distance intervals, no additional reflectance is found until a height of 3.0 mils is achieved. At this level, a higher reflectance intensity indicates that copper is present 3.0 mils from the initial reference level I. The relative height of the copper line is thus 3.0 minus 1.0, or 2.0 mils.

As the optical system continues to scan the sample, the substrate 30 warps upwardly in this example to 1.5 mils, shown at reference numeral 84. The copper height is proportionally displaced from the initial reference level I and measures 2.0 mils at all locations along the one-inch long length of the light slit 34. If the substrate 30 warps significantly upward over a substantial linear distance, it will be necessary to normalize the base line 80 so that the height of the upper surface copper line 82 will remain within the range of analysis. Similarly, if the substrate 30 warps significantly downward over a substantial linear distance, it will be necessary to normalize the base line 80 so that the height thereof will remain within the range of analysis.

Referring now again to FIG. 2, when a light slit 34 is directed through the lens 32 to the substrate 30, the CCD 38 is adapted to receive the reflected light, as hereinabove described. The CCD 38 generates a signal that varies with the intensity of the light received.

Connected to the CCD 38 is an electrical circuit, not shown in FIG. 2, for analyzing the signal generated by the CCD 38 in response to the intensity of the reflected light. This circuit, described more fully hereinbelow, is capable of distinguishing the CCD signal and classifies it according to one of three conditions: that which represents a substantially zero level of reflectance; that which represents a relatively low reflectance level; and that which represents a relatively high level of reflectance.

Two threshold levels are required to separate the three aforementioned reflectance levels: the first threshold level separates the substantially zero reflectance level from the relatively low reflectance level, and the second threshold level separates the relatively low reflectance level from the relatively high reflectance level.

The first threshold represents reflectivity of the upper surface of the substrate 30 while the second threshold represents reflectivity of the upper surface of copper lines. Accordingly, reflectance intensity below the first threshold level indicates that the upper surface of the substrate 30 has not been reached by the light source/CCD 38 combination. Likewise, reflectance intensity higher than the first threshold level (but lower than the second threshold level) indicates that the light slit 34 is reflected by the upper surface of the substrate 30. Finally, reflectance intensity higher than the second threshold level indicates that the copper line reflects the light slit 34.

The intensity of the reflected light beam is a function of the material that reflects it. Copper reflectivity is, of course, substantially greater than substrate reflectivity. By setting appropriate threshold levels, the upper surface of the substrate 30 and of the copper lines 31 can be detected and differentiated with respect to one another.

Correlating this identification of material with the height at which each threshold level is reached results in data that can be used in accurately determining the height of the copper lines 31 with respect to the upper surface of the substrate 30. Moreover, printed circuit wiring defects can also be identified either by detecting reflected light at a height at which no reflection is expected or by failing to detect reflected light at a height at which reflection is expected.

Figure 9:
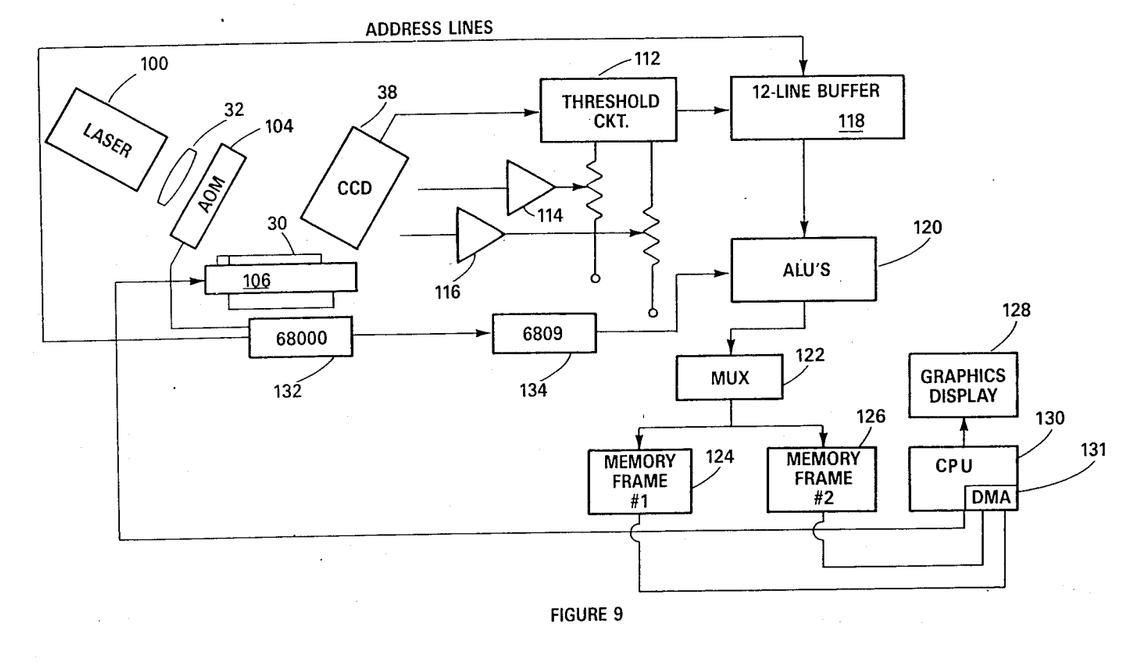
FIG. 9 is a block diagram of the detecting and measuring system in accordance with the present invention.

Referring now also to FIG. 9, there is shown a block diagram representation of the system in accordance with the present invention. A light source 100, such as a laser supplied by the Lexel Co. as Model No. 65, is used for illumination. A laser is preferred because it emits a bright, concentrated light and it can be chosen to emit a light frequency optimally matched to the materials tested.

The optical lens assembly 32 forms the light slit 34, as hereinabove described. Mounted in close proximity to the optical lens assembly 32 is an acousto optic modulator (AOM) 104, such as Model No. AOM-80 manufactured by Intraaction Co., which is an electro-optical device used to deflect the light slit 34.

A numerically controlled table 106 is provided to support a printed circuit board 30 under test and to move the board 30 along both an X-axis and a Y-axis. The CCD imaging device 38 is provided to receive light reflected from the board 30 and to generate a signal in response to the image, the signal adapted to vary with the intensity of the reflected light.

A dynamic threshold electrical circuit 112 is connected to the CCD 38 and receives an electrical signal therefrom. The circuit 112 has two threshold levels, as hereinabove described. One threshold level represents substrate reflectivity and the other represents copper reflectivity. The threshold levels are also dynamic. That is, they are instantaneously adjustable to account for differing reflectivity of the copper lines 31 on the same board 30. Such reflectivity variations may occur due to oxidation or due to other chemical or mechanical causes. A pre-selected analog voltage copper reflectivity level 114 is input to the dynamic threshold circuit 112. Similarly, an analog voltage substrate reflectivity level 116 is also input to the dynamic threshold circuit 112.

Connected to the dynamic threshold circuit 112 is a 12-line compression buffer 118 containing 6K bytes of memory. The buffer 118 can store video information corresponding to a predetermined number of height slices for each single line of the final image. Typically ten to twelve 2048×1 pixel height slices are stored in this buffer 118, but it should be understood that the size and use of this buffer 118 is a matter of design and can be adjusted according to individual system parameters and requirements.

Two bits of reflectance information per pixel are stored in the 12-line buffer 118. The two bits of information are required in the preferred embodiment to represent each reflectance category uniquely for each pixel. In the preferred embodiment, a pixel having the lowest reflectance or intensity level is represented by the arbitrary binary value 00. The next higher reflectance level is represented by the binary value 01, and the highest reflectance level is represented by the binary value 11. Of course, it should be understood that the number of bits required is dependent upon the number of threshold levels being analyzed which, in turn, depends upon the material under test. Different types of material, such as silver, platinum or gold, reflect different amounts of light. Similarly, different conditions of one material (impurities, oxides and the like) also reflect different intensities of light. Thus, in certain systems more than two binary bits of information may be needed to differentiate and identify all required intensity levels of reflectance. The binary value scheme chosen for these bits may, of course, be arbitrarily set by those skilled in the computer programming art.

Analysis circuitry 120 is used to compress height data into one line of data. The height slices are analyzed to determine copper line heights by dividing each slice into columns and counting the slices between the substrate 30 and the copper 31. To increase processing speed, Arithmetic Logic Units (ALU's), such as are supplied by Texas Instruments as Model Number 74S181, can be incorporated in the analysis circuitry 120. Each ALU is used to perform arithmetic operations such as addition, subtraction and comparison to analyze one or more of the columns to determine copper height therein. The ALU's operate in parallel in the preferred embodiment to increase throughput.

A multiplexer 122 is connected to identical memory frame devices 124 and 126. The memory frame devices 124 and 126 each store a 2K×2K video pixel image. A frame of video appears as an image of one square inch of the tested substrate in the preferred embodiment. Each memory frame device 124 and 126 is a stand alone unit capable of storing and individually addressing the required 4,194,304 (2048×2048) pixels of information.

The pixel data stored in the memory frame devices 124 and 126 is available for further analysis by a human inspector or by a computer operating under either a rules driven or a data driven procedure.

The memory frame devices 124 and 126 are connected to a CPU 130 such as any personal computer having direct memory access (DMA) 131 capability. The CPU 130 allows data stored in each memory frame device 124 and 126 to be unloaded therefrom sequentially.

A commercially available graphics display card 128, supplied by Control Systems Co. under the trademark ARTIST I, is connected to the CPU 130. The primary purpose of the graphics display is for diagnostic evaluation and development. It need not be used in the analysis of the image by a computer. The graphics display card 128, under CPU 130 control, converts height information into a topographic representation much like a topographic map. The differing height information can be represented by different colors. The colors are uniquely identified by combinations of 3 bits generated by the ALU's 120 and transferred to the multiplexer 122. Three bits of height information are capable of representing eight colors, each one corresponding to a unique height. A1

The eight colors may also be used to reperesent seven unique and individual heights in the event that a circuit feature appears at the same height as does the substrate upper surface. In that case, one color may be used to represent the upper substrate surface and another may be used to represent the circuit feature at the same height, while the remaining colors can represent, respectively, six other discrete heights.

A signal output from the CPU 130 also operates the numerically controlled table 106 to move the board 30 along the X-axis, the Y-axis or both, as required.

A microprocessor 132, such as a Motorola Model No. 68000 16-bit microprocessor, is provided to control address lines input to the 12-line compression buffer 118 and to control one or more 8-bit microprocessors 134, such as Model No. 6809 connected thereto. The microprocessors 134 coordinate the activities of the ALU's 120 that perform piece-wise columnization to compress height data. The microprocessor 132 also controls the AOM 104 to deflect the light slit 34 (FIG. 2).

Figure 10:
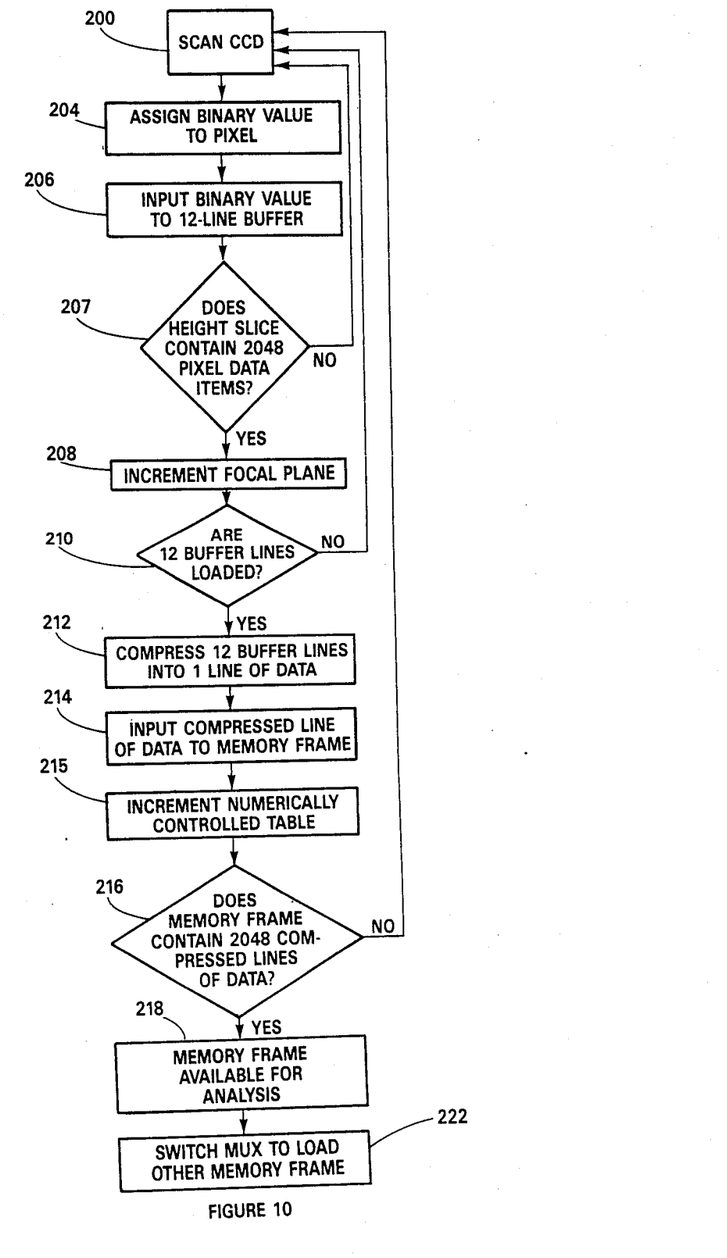
FIG. 10 is a flow chart of the inventive process for use with the detection and measuring system in accordance with the present invention.

Referring now also to FIG. 10, there is shown a flow chart of the steps of the process used in carrying out the present invention.

In operation, the laser 100 generates a coherent beam of light through the optical lens assembly 32. The optical lens assembly 32 shapes this beam of light into a slit which is directed through the AOM 104 to impinge on the circuit board 30 and the circuit features thereon. The CCD 38 is focused at a plane substantially parallel to the plane of the circuit board 30 and slightly below the upper surface thereof, step 200. A signal is generated by the CCD 38 in response to reflected light, if any, and applied to the dynamic threshold circuit 112. The signal generated by the CCD 38 is input to the dynamic threshold circuit 112 on a piecemeal basis.

The dynamic threshold circuit 112 generates a signal dependent upon the signal received from the CCD 38. The dynamic threshold circuit 112 analyzes the input signal and determines: whether it is below the first threshold (representing light reflected from the upper surface of the substrate 30); whether it is above the second threshold (representing light reflected from the upper surface of the circuit feature 31); or whether it is between the two aforementioned thresholds.

A binary value is assigned by the dynamic threshold circuit 112 to each pixel data item, step 204. The binary values are then transferred from the threshold circuit 112 to the 12-line compression buffer 118 for storage therein, step 206.

A counter in the 12-line buffer 118 determines whether the height slice is complete (i.e., whether it contains 2048 pixel data items), step 207. If the height slice is not complete, the CCD 38 again scans light reflected by the board 30, step 200.

The focal plane is then incremented, step 208, by modulating the AOM 104. The microprocessor 132 directs the AOM 104 to deflect the light slit 34 (FIG. 2) that impinges on the printed circuit board 30 and, in conjunction with the CCD 38, focuses the light slit 34 along different planes parallel to the printed circuit board plane, incrementally raising the focused planes from the initial lowest plane (level 1) to the uppermost plane (level 12) above the expected upper surface of the circuit feature 31.

The 12-line compression buffer 118 continues to be loaded. If the buffer 118 is not completely full, step 210, scanning operations continue, step 200. When all lines in the buffer 118 are loaded, step 210, the data from the buffer 118 is transferred to the ALU's 120 and compressed thereby into one line of information, step 212.

The compressed lines of data are transferred to the multiplexer 122 and thence to one of the memory frame devices 124 or 126, step 214. The numerically controlled table 106 is incremented and repositioned under direction of the CPU 130, step 215. The first memory frame device 124 has a capacity for 2048 compressed lines of data. If the memory frame device 124 is not full, step 216, scanning continues, step 200. When the first memory frame device 124 contains 2048 compressed lines of data, step 216, however, the data in that memory frame device 124 may be analyzed, step 218. Scanning then continues from step 200 and the system begins analysis of the next set of twelve levels. Thus, over a period of time, the entire printed circuit board 30 is inspected for each of twelve plane levels.

As new pixel data items are received by the CCD 38, the threshold circuit 112 assigns binary values to each pixel data item and loads the 12-line compression buffer 118, which in turn supplies the data to the ALU's 120 for compression. At this point, the microprocessor 132 generates a signal to the multiplexer 122, which switches between the first memory frame device 124 and the second memory frame device 126 when 2048 compressed lines of image data have been stored in the first memory frame device 124, step 222.

The second memory frame device 126 fills up in due course until 2048 compressed lines of data are stored therein, step 216. The multiplexer 122 then switches the ALU 120 output back to the first memory frame device 124, step 222. In this way, the multiplexer 122 loads memory frames 124 and 126 in ping pong fashion, thus increasing throughput of the system. While one memory frame device 124 is being loaded with ALU compressed data, the data stored in the other memory frame device 126 can be accessed and analyzed by a separate image analysis system, not shown. The CPU 130 can DMA access either memory frame device 124 or 126 when that particular memory frame device is not being filled by data from the ALU's 120.

More than two memory frame devices may be used if the image analysis system operates at a significantly slower rate than the ALU/memory frame device subsystem. Similarly, only one memory frame device need be used if the image analysis system connected thereto operates on a FIFO or partial memory access basis and responds quickly enough to be compatible with the ALU/memory frame device subsystem.

The microprocessor 132 also supplies address information correlating to the AOM 104 plane under analysis to the compression buffer 118. In this way, the data from each plane level under analysis can be correlated with the dynamic threshold circuit 112 and the threshold levels therein.

Since other modifications and changes varied to fit particular operating requirements and environments will be apparent to those skilled in the art, the invention is not considered limited to the example chosen for purposes of disclosure, and covers all changes and modifications which do not constitute departures from the true spirit and scope of this invention.

What is claimed is:

1. A non-contact system for detecting printed circuit wiring defects and for measuring circuit feature height relative to a substrate comprising:
   (a) a laser for illuminating said substrate and circuit features thereon;
   (b) a charge coupled device (CCD) having a plurality of elements disposed therein for receiving laser energy reflected from a predetermined area on said substrate and circuit features thereon and wherein said plurality of CCD elements are individually and simultaneously activated, said CCD being disposed proximate said substrate and circuit features thereon and operatively related thereto, said CCD being capable of:
      (i) substantially instantaneously receiving laser energy reflected from said substrate and cirucit features thereon; and
      (ii) generating a signal in response thereto, said signal varying with the intensity of said reflected laser energy; and
   (c) automatic analyzing means operatively connected to said CCD for correlating said signal received therefrom to a measurement representative of height of said cirucit features on said substrate and relative thereto, said analyzing means being adapted to analyze laser energy received by each of said plurality of CCD elements for a predetermined number of cycles so that non-linearities on said substrate and circuit features thereon are detected.

2. The system in accordance with claim 1 further comprising:
   (d) positioning means for moving said CCD relative to said substrate.

3. The system in accordance with claim 1 wherein said analyzing means comprises a first memory for storing data representative of said signal generated by said CCD.

4. The system in accordance with claim 3 wherein said analyzing means further comprises calculating means for using said data stored in said first memory to determine the height of said circuit features, said calculating means being operatively connected to said first memory.

5. The system in accordance with claim 4 wherein said analyzing means further comprises a second memory operatively connected to said calculating means for storing data representative of dimensions of said circuit features.

6. The system in accordance with claim 5 wherein said second memory comprises at least two memory frame devices for facilitating storage of said data representative of said dimensions of said circuit features.

7. The system in accordance with claim 6 wherein each of said memory frame devices is sequentially accessed according to a predetermined schedule.

8. The system in accordance with claim 1 further comprising:
   (d) means for moving said laser energy discretely through a plurality of focal planes over at least the field of view relative to said CCD.

9. The system in accordance with claim 8 wherein said laser energy moving means is an acousto-optic modulating device.

10. A non-contact system for detecting printed circuit wiring defects and for measuring circuit feature height relative to a substrate comprising:
    (a) a radiant energy source for illuminating said substrate and circuit features thereon;
    (b) scanning means disposed proximate said substrate and circuit features thereon and operatively related thereto, said scanning means being capable of:
       (i) substantially instantaneously receiving radiant energy reflected from said substrate and circuit features thereon; and
       (ii) generating a signal in response thereto, said signal varying with the intensity of said reflected energy; and
    (c) automatic analyzing means operatively connected to said scanning means for correlating said signal received therefrom to a measurement representative of height of said circuit features on said substrate and relative thereto, wherein said analyzing means is adapted to detect three categories of reflected radiant energy intensity, said categories being bounded and defined by two threshold levels and wherein one of said threshold levels separates the intensity of background radiant energy from the intensity of radiant energy reflected from said substrate.

11. The system in accordance with claim 10 wherein the other one of said threshold levels separates the intensity of radiant energy reflected from said substrate from the intensity gradiant of energy reflected from said circuit features, whereby the presence of said circuit features is detected.

12. A method for detecting printed circuit wiring defects and measuring the height of the upper surface of a circuit feature relative to a substrate having a base and an upper surface, the steps comprising:
    (a) projecting radiant energy onto said substrate and circuit feature thereon;
    (b) providing a scanning means for receiving reflected radiant energy;
    (c) moving the radiant energy relative to said substrate such that said radiant energy is in focus at an initial focal plane below the base of said substrate and substantially parallel thereto, relative to said scanning means;
    (d) generating a signal in response to said reflected radiant energy, said signal being adapted to vary with the intensity thereof;
    (e) correlating said signal to a reference level of intensity representative of reflectivity;
    (f) moving said radiant energy relative to said substrate such that said radiant energy is in focus at a plane above said initial focal plane and substantially parallel thereto;
    (g) repeating steps (d) through (f) until the focused plane is above the level of the upper surface of said circuit feature; and (h) correlating said signals generated in step (e) to measurements representative of the height of said circuit features and printed circuit wiring defects.

13. The method in accordance with claim 12, the steps further comprising storing a value representative of the location of the focused plane relative to said initial focal plane for each plane scanned thereby.

14. The method in accordance with claim 13, the steps further comprising subtracting the value representative of said initial focal plane from the value representative of the plane at the upper surface of said substrate to obtain a substrate upper surface height above said initial focal plane.

15. The method in accordance with claim 19, the steps further comprising periodically normalizing the value representative of the height of the upper surface of said substrate relative to said initial focal plane.

16. The method in accordance with claim 19, the steps further comprising subtracting the value representative of said initial focal plane from the value representative of the plane at the upper surface of said circuit feature to obtain a value representative of the height of said upper surface of said circuit feature relative to said initial focal plane.

17. The method in accordance with claim 16, the steps further comprising subtracting the value representative of the substrate upper surface height above said initial focal plane from said value representative of the height of the upper surface of said circuit feature relative to said initial focal plane to obtain a value representative of the height of the upper surface of said circuit feature relative to the upper surface of said substrate.

18. The method in accordance with claim 13, the steps further comprising subtracting the value representative of the focal plane at the upper surface of said substrate from the value representative of the focal plane at the upper surface of said circuit feature to obtain a value representative of the height of the upper surface thereof relative to said upper substrate surface.

19. The method in accordance with claim 18, the steps further comprising normalizing the value representative of the height of the upper surface of said substrate relative to said initial focal plane as required.

* * * * *